Figure 1:
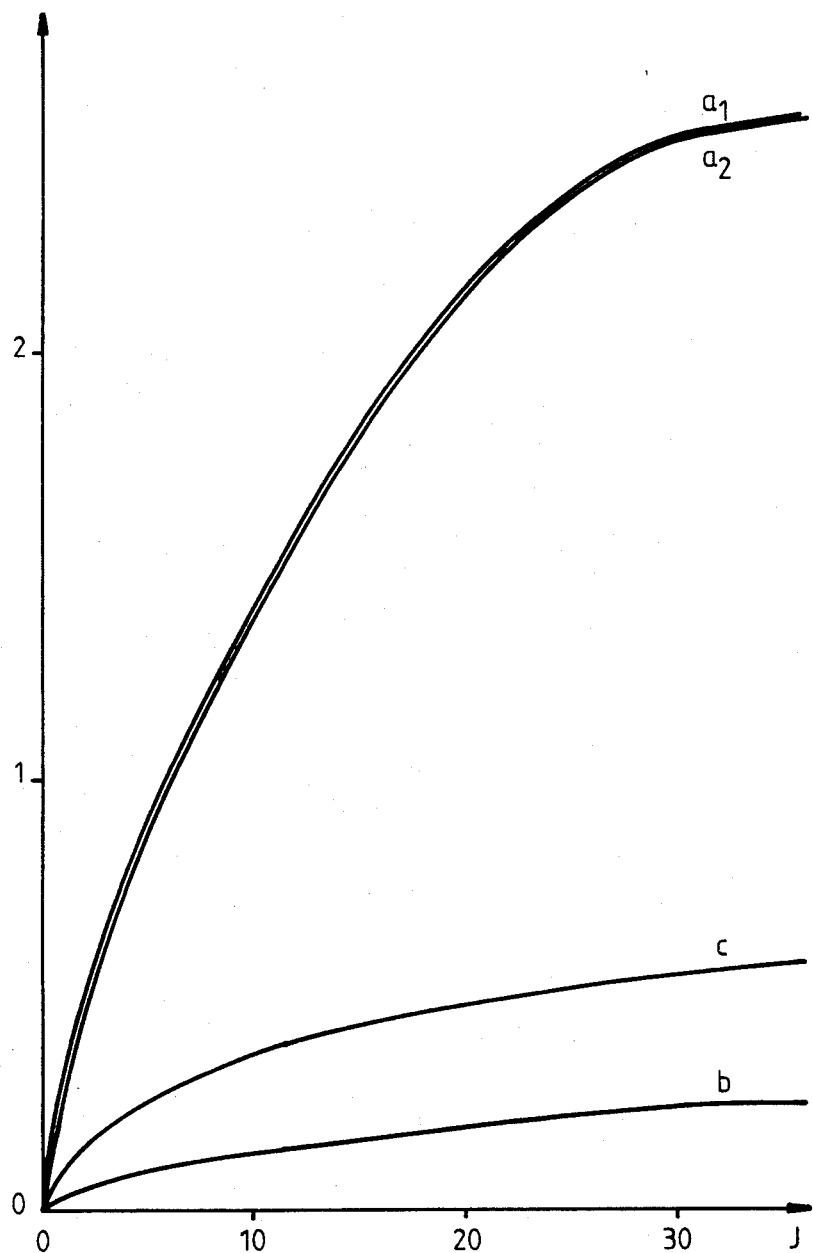

United States Patent [19]

Weiss et al.

[11] Patent Number: 4,619,824
[45] Date of Patent: Oct. 28, 1986

[54] METHOD FOR REDUCING THE WATER DESORPTION OF AN ACTIVE COMPOSITION CARRIED BY A SUPPORTING MEDIUM

[75] Inventors: Richard Weiss, Chartres; Hubert Delagneau, Mainvilliers, both of France

[73] Assignee: Reckitt & Colman, S.A., Massy Cedex, France

[21] Appl. No.: 556,245

[22] PCT Filed: Mar. 4, 1983

[86] PCT No.: PCT/FR83/00042
§ 371 Date: Nov. 3, 1983
§ 102(e) Date: Nov. 3, 1983

[87] PCT Pub. No.: WO83/03056
PCT Pub. Date: Sep. 15, 1983

[30] Foreign Application Priority Data
Mar. 4, 1982 [FR] France ............................. 82 03599

[51] Int. Cl.$^4$ ........................ A61L 9/01; A61L 9/04
[52] U.S. Cl. .................................... 424/16; 424/76; 424/65; 424/25
[58] Field of Search ....................... 424/76, 65, 25, 16

[56] References Cited

FOREIGN PATENT DOCUMENTS
1590898 4/1970 France .
1603822 7/1971 France .

Primary Examiner—John Kight
Assistant Examiner—M. L. Moore
Attorney, Agent, or Firm—Browdy and Neimark

[57] ABSTRACT

The method comprises the treatment of the composition and/or the substrate with at least one compatible polar substance selected among compounds which are susceptible, on one hand, to impart finally to the substrate or to said composition an ionic charge opposite to that of the other one or to excite the ionic charge inherent to the treated composition and/or substrate if that charge is already opposite to that of the other one and, on the other hand, to obtain at the same time a hydrophilic/lipophylic balance (HLB) such that the surface tension of the couple supporting medium-composition is lower than the surface tension of the couple supporting medium-water.

15 Claims, 3 Drawing Figures

METHOD FOR REDUCING THE WATER DESORPTION OF AN ACTIVE COMPOSITION CARRIED BY A SUPPORTING MEDIUM

This invention relates to a process to prevent water desorption in a chemical liquid active substance carried on an absorbing support.

Various cases are known, in which one or more chemical substances are applied on to natural or synthetic substrates in particular for preservation and/or protection thereof from external aggressions of chemical, biological or other nature. There can be cited for example the protection of plants, stones, wood, leather, living organisms, body hygiene, and the like.

Many other cases are known, wherein one or more chemical substances are applied on to natural or synthetic substrates, in particular, for realizing an exchange with environment, the surrounding medium, or any other support. There can be cited for example the case of the progressive release of a perfume or an active substance, for deodorizing environments, desinfection of atmospheres, fight against insects.

In several applications, however, the substrates carrying the active substance is permanently, periodically or else, accidentally exposed to the action of water.

In many cases, such water provokes progressive, often rapid, desorption of the active principles in the substrate, thereby resulting in considerable loss of active substance and decrease with time of the efficiency of the system. To prevent or at least reduce any consequences of such phenomenon, processes or means substantially comprising hydrofugation and water proofing have been resorted to. Such means and processes may be classified into three main categories:

(1) Preliminary hydrofugation of the support before application of the active principle(s), the hydrofugating agent being applied directly or in solution in a solvent, or else, in emulsion in water.

(2) Application of the active principle(s) on to the substrate followed by hydrofugation, with the hydrofugating agent being applied directly or in solution in a solvent, or else, in emulsion in water.

(3) Incorporation of a hydrofugating agent into the active substance(s) as a solution or emulsion, then application of such composition onto the substrate.

Such processes, however, have major deficiencies in a great number of cases:

(1) Generally, in order to fight the consequences of water desorption in the active principles, it is necessary to incorporate large quantities of hydrofugating agent thereinto, hence limiting the quantities of active substance(s) to be carried by the substrate.

(2) The process for preliminary hydrofugation of the support through incorporation of the hydrofugating agent thereinto as a solution in a solvent or as an emulsion always requires an operation for removing the vehiculent, which can only be expensive, before application of the active principle(s). Moreover, when a water emulsion of the hydrofugating agent is resorted to, the emulsifier used generally remains on the substrate and provokes substantial reduction in the qualitative properties of the hydrofugation.

(3) When hydrofugation takes place after application of the active principle(s) onto the substrate, the same deficiencies as mentioned above are to be observed. Moreover, when the substrate is to carry volatile compositions, for the progressive evaporation thereof into the atmosphere, the required quantities of hydrofugating agent which must be used are such that in many cases they modify normal evaporation of such compositions unless they should totally stop it.

(4) Very often, the known hydrofugation processes do not stop or modify the water desorption phenomenon in the active principle(s) carried by the substrate.

(5) In many cases, the known hydrofugation processes are not applicable in particular when it is desired to treat substrates such as animal tissues, vegetal tissues, human tissues, or else, natural substrates or materials, of which the original conditions or aspect should not be modified.

The Applicant has now discovered fortuitously and surprisingly that it was possible to reduce to minimum water desorption in an active principle carried by a substrate by acting by means known in themselves upon the respective ionic charges of the components in the assembly such that the final ionic charge of the substrate is opposite to that of the composition of active principle(s), on the one hand, and on the other hand, on the lipophilous/hydrophilous balance (HLB) of the active principle composition so as to obtain in the final system a surface tension in the support and active principle composition couple lower than the surface tension of the absorbing support and water couple.

In this description it is meant by support any porous substance capable of absorbing or adsorbing a liquid substance independently of how much quantity of this substance was absorbed or adsorbed.

To obtain this result there is provided according to the invention a simple and economical process for reducing to minimum water desorption in an active chemical composition carried by a substrate when such an assembly is brought into contact with an aqueous medium in a permanent, periodical or accidental manner, such process being characterized by comprising the steps of treating the composition and/or the substrate with at least one compatible polar substance selected from the group comprising compounds capable of finally conferring either to the substrate or said chemical active composition an ionic charge opposite to that of the other or of exalting the ionic charge inherent to the composition and/or to the treated substrate if such charge is already opposite to that of the other, on the one hand, and on the other hand, of simultaneously obtaining a hydrophilous/lipophilous balance (HLB) such that the surface tension of the support and active composition couple is lower than the surface tension of the support and water couple.

Thus, the polar treatment substance(s) are selected depending on the ionic character of each of the constituents of the final system to be achieved, and on the lipophilous hydrophilous balance of the active chemical substance or composition.

The process according to the invention therefore consists either of treating the active chemical substance or composition by at least one agent compatible with such substance or composition and which will be selected so as to give the resulting chemical composition an opposite polarity to that of the substrate or of treating the substrate to give it an opposite polarity to that of the active chemical composition, the polarity of the latter being itself modifiable as mentioned above to give it the desired polarity. In particular, when the active chemical substance or composition has itself a specific polarity the treating agent might be selected only with a view to modifying the polarity of the substrate either to reverse the natural polarity of the latter to render it opposite to that of the active chemical composition or else to increase the natural affinity of the substrate when its ionicity is already opposite to that of the active chemical composition. Similarly, when it is desired for one or the other reason to use a treating agent of a given polarity and to apply the composition containing such agent onto an electrically neutral support or support having the same polarity as that of said agent, a treatment can be carried out to give such support an opposite polarity to that of said composition. Therefore, according to the invention, the above-mentioned treatment(s) by means of the polar substance(s) can be effected before, during or after deposition of the active composition onto the substrate.

According to one characteristic of the invention, the quantity of polar substance should be sufficient to obtain both of the conjugated conditions, i.e. polarity and HLB, without substantially modifying the relative quantities of the constituents in the final system, or the essential characteristics of such constituents or their mode of activity, in particular, that of the active chemical substance or composition. Preferably, such quantity will be relatively low as compared to the active composition.

In this way one does not modify the nature of the body(bodies) present or the concentrations thereof or the quantities of active princples absorbable by the substrate or the mode of activity of the active principle(s) carried by the substrate. These respected conditions are the more interesting in the specific case of volatile substances the evaporation characteristics of which are taken advantage of for treating an environment. In this case, actually, such evaporation characteristics must not be modified or opposed as might be the case when resorting to hydrofugation of the substrate to fight water desorption, before or after impregnation of the substrate with the active substance or composition.

The invention also covers the application of the process for the realization of water resisting systems containing active substance compositions as well as means for carrying out such process, i.e. the active substances and/or the substrates treated to this end.

Compounds belonging to the following classes may be cited as examples of treating agents suitable for the process according to the invention:

(1) In the case of negative charge supports when the impregnation substance has no specific polarity:
the compounds containing at least one hetero-atom $P^+$, $O^+$, $S^+$, or $N^+$, and at least an alkyl long chain of at least 8 carbon atoms such as quaternary ammonium salts, imidazoline salts, phosphonium salts, oxonium salts, the fatty amines and derivatives thereof.

(2) In the case of positive charge supports, when the impregnation substance has no specific polarity:
the compounds containing at least one group of an anionic character such as a carboxylic, sulfonic, phosphoric, sulfuric group, and at least one alkyl long chain of at least 8 carbon atoms such as alkylphosphonic, alkylsulfuric, alkylsulfonic, alkylcarboxylic acids.

(3) In the case where the impregnation substance or composition has a specific polarity:
(a) negative specific polarity, with the support being of a positive charge:
mono or polyfunctional compounds such as organic bases, mineral bases, compounds of at least bifunctional character having at least one group of negative ionic character and having moreover a positive ionic character higher than those of the ionic group of the support such as monocarboxylic polyamines, peptides, sulfobetaines, (a') negative specific polarity, with the support being of a negative charge:
the bi or polyfunctional compounds comprising at least two positive ionic groups such as polyamines, quaternary polyammoniums, (b) positive specific polarity, with the support being of a positive charge:
the compounds comprising at least two negative ionic groups such as polyacids, (b') positive specific polarity, with the support being of a negative charge:
the mono or polyfunctional compounds such as the mineral acids and the organic acids, those compounds with at least bifunctional character having at least one group of positive ionic character having moreover a negative ionic character higher than those of the ionic groups of the support such as monoamine polyacids, amino-acids, peptides, sulfo-betaines.

The following table illustrates the process according to the invention.

| S | I | $A_S$ | $A_I$ |
|---|---|---|---|
| 0 | 0 | + | − |
|   |   | − | + |
|   | + | − |   |
|   | − | + |   |
| + | 0 |   | − |
|   | + | − |   |
|   | − | ↑+ |   |
|   |   | ↑+ | ↑− |
| − | 0 |   | ↑− |
|   | + | ↑− | + |
|   |   |   | ↑+ |
|   | − | ↑− | ↑+ |
|   |   | + |   |
|   |   |   | + |

In this table, column "S" shows the polarity of the substrate, column "I" that of the impregnation substance or composition, column "$A_S$" the polarity of the treating agent of the substrate, and column "$A_I$" that of the treating agent of the impregnation substance or composition; the arrows show the increase of the resulting polarity.

The interest and advantages of this invention will appear more clearly from the following description and the experimental examples presented for illustration purposes and not at all limitatively. These examples illustrate the application of the invention in the following cases:

Fixation of a composition of active substances without any specific ionic character:
onto an absorbing support having a negative ionic character,
onto an absorbing support having a positive ionic character.

Fixation of a composition of active substances having a specific ionic character through modification of the ionicity of the absorbing support.

Fixation of a composition of active substances without any specific ionic character by an additive defined by modifying the ionicity of the absorbing support.

The method generally used is the following: The compositions of active substances to be tested are coloured if need be by means of water-immiscible colorants, then according to the present invention, are impregnated on the absorbing support, and thereafter, finally immersed in water maintained at the ambient temperature.

Desorption of the active substance composition is evaluated visually with time. It is marked as:
0: no desorption,
1: low desorption
2: partial desorption,
3: almost total desorption.

EXAMPLES

Example 1

Fixation of an active liquid substance composition without any specific ionic character on a support having a negative ionic character Material Absorbing support: For illustration example of an absorbing substance, a cellulose plate has been chosen (available on the market under the designation of "Spartose OM-22" of the firm: Société La Rochette Cenpa)

Composition of active substances: dodecane (available on the market under the designation "Solis" of Société B.P.)

Additive: quaternary distearyl dimethyl ammonium chloride

Results:

The additive has been introduced into the active substance composition at the rate of 2% by weight.

The results are contained in the following Table I:

TABLE I

| Conditions | Time in mn | | | | |
|---|---|---|---|---|---|
| | 1 | 15 | 30 | 45 | 60 |
| Composition alone | 1 | 2.5 | 2.5 | 2.5 | 2.5 |
| Modified composition | 0 | 0 | 0 | 0 | 0 |

Example 2

Fixation of an active substance composition without any specific ionic character on an absorbing support having a positive ionic character Material:

Absorbing support: cationic resin, reference "Ionenaustauscher III" of the firm Merck Active substance composition: dodecane, reference "Solis" (B.P.)

Additive: oleic acid.

Results:

In this Example, the absorbing support was treated separately by the additive in the following manner:

Treatment for 30 minutes by an alcoholic solution with 2% by weight of oleic acid, or by alcohol for the reference test, filtration, then drying to constant weight, before impregnation with the active substance composition.

Desorption of the active substance composition was evaluated after two hours of immersion.

The results are contained in the following Table II:

TABLE II

| Conditions | Desorption after 120 mn |
|---|---|
| Untreated support | 3 |
| Treated support | 0 |

Example 3

Fixation of an active substance composition having a specific ionic character through modification of ionicity of the absorbing support Material:

Absorbing support: cellulose plate, reference "Spartose OM-22" of the firm Société La Rochette Cenpa.

Active substance composition: methyl salicylate.

Modification of the support ionicity:

The specific negative ionicity of the support is increased by a treatment with a strong inorganic acid. The support is immersed for 30 minutes in a solution with 5% by weight of technically pure hydrochloric acid, rinsed with demineralized running water for 1 minute and dried to constant weight.

The results are contained in the following Table III:

TABLE III

| Conditions | Time in mn | | | | |
|---|---|---|---|---|---|
| | 1 | 15 | 30 | 45 | 60 |
| Untreated support | 1 | 1.5 | 2 | 2.5 | 2.5 |
| Treated support | 0 | 0.5 | 0.5 | 1 | 1 |

Example 4

Fixation of an active substance composition without any ionic specific character by an additive defined by modifying the ionicity of the absorbing support Material:

Absorbing support: cellulose plate, reference "Spartose OM-22" (Société La Rochette Cenpa).

Active substance composition: perfuming composition of the Pine type, reference "Tanalis" (Société Naarden)

Additive: oleic acid.

Modification of the support ionicity:

The support is treated so as to give it a positive ionic character opposite to that of the selected additive.

The support is treated for 30 minutes with a solution of 5% by weight of a technically pure hydrochloric acid, rinsed by demineralized running water for 1 minute, then treated for 30 minutes by a solution of 5% by weight diamine ethylene, rinsed with demineralized running water for 1 minute, then finally dried to a constant weight.

The additive was introduced into the active substance composition at a concentration of 2% by weight.

Results:

the results are contained in the following Table IV:

TABLE IV

| Conditions | Time in mn | | | | |
|---|---|---|---|---|---|
| | 1 | 15 | 30 | 45 | 60 |
| Untreated cellulose | | | | | |
| Pine type reference composition | 0.5 | 2 | 2.5 | 3 | 3 |
| Pine type composition treated with oleic acid | 1 | 2.5 | 3 | 3 | 3 |
| Treated cellulose | | | | | |
| Pine type reference composition | 1 | 2 | 2.5 | 3 | 3 |
| Pine type composition treated | 0 | 0.5 | 1 | 1.5 | 1.5 |

TABLE IV-continued

| Conditions | Time in mn | | | | |
|---|---|---|---|---|---|
| | 1 | 15 | 30 | 45 | 60 |
| with oleic acid | | | | | |

CONCLUSIONS

The results obtained show clearly that this invention is capable of preventing or reducing to minimum the water desorption phenomenon in active substance compositions impregnated on absorbing supports, and therefore preventing or slowing down the elimination of said active substance composition from said supports when these are brought into contact in a permanent, periodical or accidental manner with water, or diluted aqueous solutions.

Furthermore, in order to clearly demonstrate the technical and economical advantages of this invention, the Applicant has proved:

that it is possible to prevent water desorption in an insecticide composition impregnated on an absorbing support and therefore to realize new types of insecticidal that may be exposed to rain or moisture without losing their efficiency, that it is possible to prevent water desorption in perfuming compositions impregnated on an absorbing support and therefore to realize new types of ambiance deodorants (or reodorants) products insensitive to water or moisture which may for example be secured under the rim of toilet bowls.

Example 5

Fixation of an insecticide composition onto an absorbing support

The fixation of the insecticidal composition onto the absorbing support has been evaluated according to the above-described immersion method.

Material:

Absorbing support: cellulose plate, reference "Spartose OM-22" of Société La Rochette Cenpa Insecticidal composition: composition that may be used for insecticidal treatment of plants.

| Formula in parts by weight: | |
|---|---|
| Pyrethrine | 0.05 |
| Piperonyl butoxide | 0.25 |
| Rotenone | 0.025 |
| Chloropropylate | 0.05 |
| Dichlone | 0.1 |
| Dinocap | 0.05 |
| Lindane | 0.1 |
| Dichloromethane | 26.7 |

Additive: quaternary distearyl dimethyl ammonium chloride.

Results:

The additive was introduced into the insectidical composition at the low rate of 5% by weight.

The results are contained in Table V hereinbelow:

TABLE V

| Conditions | Time in mn | | | | |
|---|---|---|---|---|---|
| | 1 | 15 | 30 | 45 | 60 |
| Reference: composition alone | 1 | 2 | 2.5 | 2.5 | 2.5 |
| Modified composition | 0 | 0 | 0 | 0 | 0 |

CONCLUSIONS

The results obtained show clearly that this invention can advantageously be applied when it is desired to prevent water desorption of insecticide compositions to be applied on absorbing supports.

Example 6

Realization of an ambiance deodorant to be secured under the rim of toilet bowls Study of water desorption in perfuming compositions impregnated on an absorbing support.

The degree of fixation of the perfuming compositions on the absorbing support was evaluated according to the above-described immersion method.

For this study complex formulated perfuming compositions and chemically defined perfumes have been used.

The compositions to be tested are coloured by means of a water-immiscible liposoluble colorant, then impregnated on the absorbing support and finally immersed in water maintained at the ambient temperature.

The desorption of the perfuming composition is evaluated visually with time.

It is noted as follows:

0: no desorption
1: low desorption
2: partial desorption
3: almost total desorption.

Material:

Absorbing support:

Cellulose plate of a negative ionic character

Reference: "Spartose OM-22" (Société La Rochette Cenpa)

Perfuming compositions:

Complex Pine type composition: reference "Tanalis" (Naarden)

Complex Floral type composition: reference "Boronia" (the firm Givaudan)

Bornyl acetate

Methyl salicylate.

Additives: Compounds comprising at least one ionic group of a cationic character Additive A: quaternary distearyl dimethyl ammonium chloride Additive B: 1-ethyl-1-stearylamido-1-ethyl-2-stearyl-imidazoline ethyl sulfate Additive C: 1-hydroxyethyl-2-heptadecenyl-imidazoline Additive D: N-stearylamine Additive E: quaternary stearyl trimethyl ammonium chloride.

The concentrations of additives used are expressed in percentage by weight relative to the perfuming composition.

Results:

TABLE VI

| Pine type perfuming composition | | | | | |
|---|---|---|---|---|---|
| | | Time in mn | | | |
| Additive | Additive concentration | 1 | 4 | 20 | 60 |
| Reference: Pine type composition | | 0.5 | 1 | 3 | 3 |
| A | 0.6 | 0 | 0.5 | 1 | 2 |
| A | 2 | 0 | 0 | 0 | 0 |
| C | 5 | 0 | 0 | 0.5 | 1 |
| D | 10 | 0 | 0 | 1 | 1 |
| E | 5 | 0.5 | 1 | 1 | 1 |

TABLE VII

Floral type perfuming composition

| Additive | Additive concentration | Time in mn 1 | 15 | 30 | 60 |
|---|---|---|---|---|---|
| Reference: Floral type composition | | 1 | 3 | 3 | 3 |
| A | 2 | 0 | 0 | 0 | 0 |
| B | 2 | 0 | 0 | 0.5 | 1 |
| C | 2 | 0 | 1 | 1.5 | 2 |

TABLE VIII

Bornyl acetate

| Additive | Additive concentration | Time in mn 1 | 15 | 30 | 60 |
|---|---|---|---|---|---|
| Reference: bornyl acetate | | 2 | 2.5 | 2.5 | 3 |
| A | 2 | 0 | 0 | 0 | 0 |
| B | 2 | 0 | 0 | 0 | 0 |
| C | 2 | 0.5 | 1 | 2.5 | 2.5 |

TABLE IX

Methyl salicylate

| Additive | Additive concentration | Time in mn 1 | 15 | 30 | 60 |
|---|---|---|---|---|---|
| Reference: methyl salicylate | | 1.5 | 1.5 | 2 | 2.5 |
| B | 2 | 0.5 | 1 | 1.5 | 1.5 |
| C | 10 | 0 | 0 | 0 | 0 |

CONCLUSIONS

These results show that the systems according to this invention limit or even totally prevent water desorption in perfuming compositions impregnated on an absorbing support and that it is therefore possible to position them under the rims of toilet bowls, without the compositions being extracted by water upon actuation of the water flush.

Study of the evaporation of perfuming compositions:

(a) When these are incorporated in known perfuming detergent blocks for toilet bowls without paradichlorobenzene and with paradichlorobenzene (P.D.C.B.);

(b) When the same compositions are secured to an absorbing support;

(c) When the same absorbing support is impregnated with perfuming compositions and additives according to the invention.

The method used is as follows:

One follows up by weighing the evaporation of the perfuming compositions incorporated in the blocks or impregnated on porous supports as to equivalent quantities and evaporation surface under constant conditions of air motion, temperature and hygrometry (20° C. 25% R.M.). In blocks containing paradichlorobenzene, the loss of weight of the perfuming composition is determined through chromatographic analysis in gaseous phase.

The evaporation curves corresponding to the following function are plotted:

$P = f(t)$, where P is the cumulated loss of weight of the perfuming composition, t is the evaporation time.

Then, there are set up the comparative Tables:
of the values of P as a function of t,
of the values $dP/dt$ as a function of t, graphically determined when $dt \rightarrow 0$.

The obtained values directly measure the potential perfuming effect of the perfuming compositions.

When the perfuming compositions are incorporated in cleansing blocks, the composition of the blocks is the following (parts by weight):

| | A | B |
|---|---|---|
| Sodium dodecyl benzene sulfonate | 50 | 50 |
| Sodium sulfate | 8.5 | 8.5 |
| Polyethylene wax | 25 | 30 |
| Paradichlorobenzene | 5 | — |
| Precipitated silica | 5 | 5 |
| Perfuming composition | 6.5 | 6.5 |
| Colorants | traces | traces |

Figure 2:
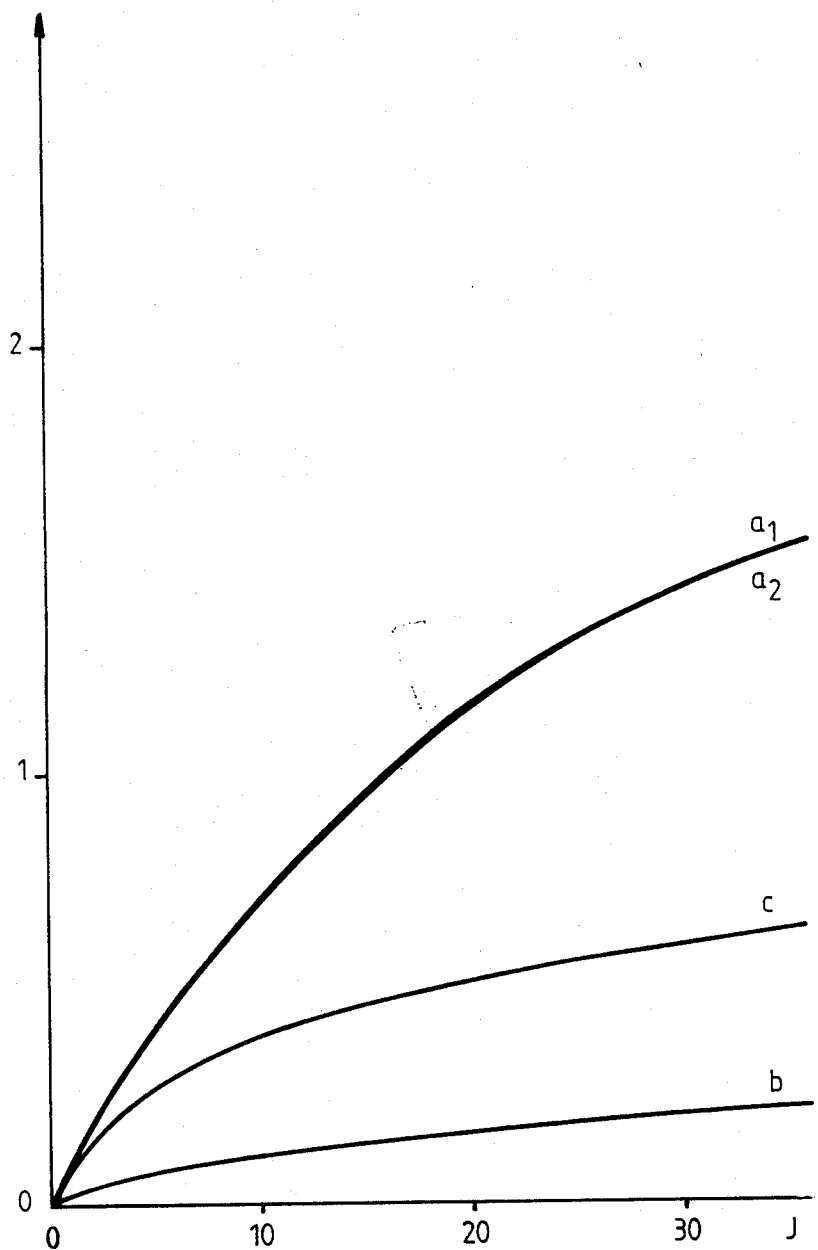
Figure 3:
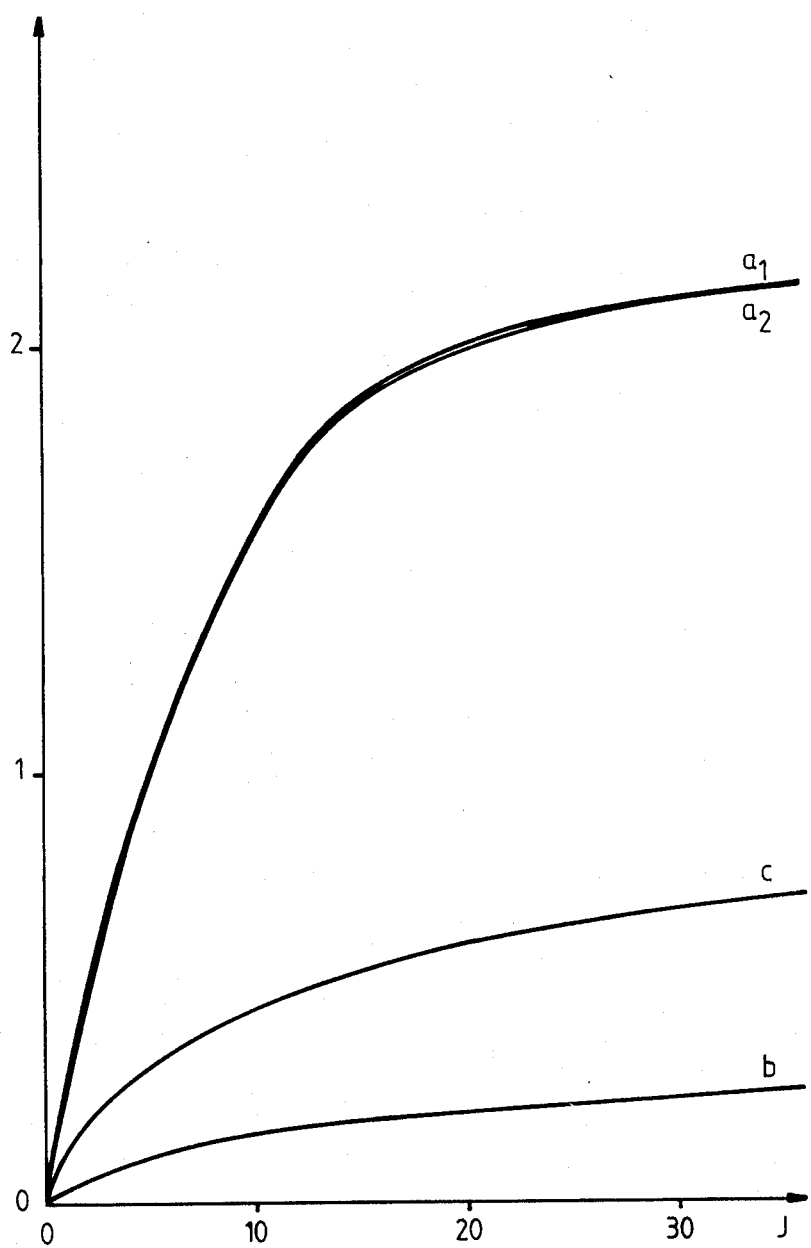

Results:

The obtained results are grouped in the evaporation curves of FIGS. 1, 2 and 3, attached herewith, and in the following Tables wherein:

$a_1$ is the perfuming composition impregnated on an absorbing support according to the invention, $a_2$ is the perfuming composition impregnated on any absorbing support, b is the perfuming composition introduced into a detergent block without paradichlorobenzene, c is the perfuming composition introduced into a detergent block containing paradichlorobenzene.

TABLE X

Pine type perfume A, weight: 2.6 g

| Evaporation time (days) | | $P = f(t)$ g | $\frac{\Delta P}{\Delta t}$ g/days |
|---|---|---|---|
| 5 | $a_1 = a_2$ | 0.92 | 0.12 |
| | b | 0.09 | 0.01 |
| | c | 0.28 | 0.03 |
| 10 | $a_1 = a_2$ | 1.4 | 0.12 |
| | b | 0.12 | 0.01 |
| | c | 0.35 | 0.03 |
| 15 | $a_1 = a_2$ | 1.84 | 0.10 |
| | b | 0.17 | 0.01 |
| | c | 0.43 | 0.015 |
| 20 | $a_1 = a_2$ | 2.16 | 0.07 |
| | b | 0.2 | 0.005 |
| | c | 0.47 | 0.01 |
| 30 | $a_1 = a_2$ | 2.5 | 0.02 |
| | b | 0.2 | 0.05 |
| | c | 0.56 | 0.007 |

TABLE XI

Floral type perfume B, weight: 2.6 g

| Evaporation time (days) | | $P = f(t)$ g | $\frac{\Delta P}{\Delta t}$ g/days |
|---|---|---|---|
| 5 | $a_1 = a_2$ | 0.42 | 0.08 |
| | b | 0.07 | 0.015 |
| | c | 0.3 | 0.03 |
| 10 | $a_1 = a_2$ | 0.74 | 0.06 |
| | b | 0.12 | 0.01 |
| | c | 0.4 | 0.03 |
| 15 | $a_1 = a_2$ | 0.96 | 0.05 |
| | b | 0.16 | 0.01 |
| | c | 0.47 | 0.02 |
| 20 | $a_1 = a_2$ | 1.16 | 0.03 |
| | b | 0.18 | 0.005 |
| | c | 0.52 | 0.02 |
| 30 | $a_1 = a_2$ | 1.45 | 0.025 |
| | b | 0.2 | 0.0025 |
| | c | 0.6 | 0.1 |

TABLE XII

Woody type perfume C, weight: 2.6 g

| Evaporation time (days) | | $P = f(t)$ g | $\frac{\Delta P}{\Delta t}$ g/days |
|---|---|---|---|
| 5 | $a_1 = a_2$ | 1 | 0.13 |
|   | b | 0.1 | 0.02 |
|   | c | 0.35 | 0.04 |
| 10 | $a_1 = a_2$ | 1.55 | 0.08 |
|   | b | 0.16 | 0.01 |
|   | c | 0.46 | 0.03 |
| 15 | $a_1 = a_2$ | 1.88 | 0.05 |
|   | b | 0.19 | 0.007 |
|   | c | 0.55 | 0.015 |
| 20 | $a_1 = a_2$ | 2.0 | 0.02 |
|   | b | 0.22 | 0.003 |
|   | c | 0.62 | 0.01 |
| 30 | $a_1 = a_2$ | 2.1 | 0.01 |
|   | b | 0.24 | 0.002 |
|   | c | 0.7 | 0.005 |

CONCLUSIONS

The results show clearly the superiority of the perfuming effect that can be obtained by means of this invention and the economic profits entailed thereby.

Organoleptic evaluation of the perfuming compositions in the normal conditions of use:

(a) When these are incorporated in perfuming detergent blocks based on paradichlorobenzene (b) When these are deposited on an absorbing support (c) When these are fixed on an absorbing support according to the present invention.

The perfuming power of the perfuming compositions is evaluated by an appropriate panel, 2 by 2, in parallel, in olfaction cabins, before and after positioning in toilet bowls, the water flushes of which are automatically actuated in accordance with the following evaluation pattern:

1: no perfuming action,
2: low perfuming action,
3: correct perfuming action,
4: good perfuming action,
5: strong perfuming action.

Results:

(a) Comparison of the perfuming power of identical cellulose plates impregnated with a perfuming composition and impregnated with the same perfuming composition according to the invention:

| | Marks obtained (average) | |
|---|---|---|
| Number of flushings | Starting | After 450 flushings (number of flushings obtained in 6 days) |
| Conventional impregnation | 3.4 | 2.7 |
| Impregnation according to invention | 3.5 | 3.8 |

(b) Comparison of the perfuming power of a perfuming composition secure according to the invention to a cellulose plate and introduced into a detergent block based on paradichlorobenzene with identical weight and evaporation surface:

| | Marked obtained (average) | |
|---|---|---|
| Number of flushings | Starting | After 450 flushings (number of flushings obtained in 6 days) |
| Cellulose impregnated | 3.75 | 3.6 |
| according to invention Perfuming detergent block | 2.9 | 2.8 |

CONCLUSIONS

The results obtained show clearly the superiority of the effect produced according to this invention as compared to the usual known processes.

It results from the foregoing that the process according to the invention can be usefully carried out generally each time it is desired to oppose the water desorption phenomenon in any composition deposited or to be deposited on a substrate, and therefore, in particular when a volatile active composition is deposited or is to be deposited on an appropriate substrate for treating environments or else when the active composition must be maintained into contact with the substrate to protect or treat the latter.

We claim:

1. A process for reducing desorption by and into water of a liquid active chemical composition carried by a substrate when such an assembly is in contact with an aqueous medium, said process comprising treating at least one of the composition or the substrate with at least one compatible polar compound which provides the substrate or said composition an opposite ionic charge to that of the other, or increases the ionic charge between the composition and the substrate if such charge is already opposite to that of the other, and simultaneously provides a hydrophilic/lipophilic balance (HLB) such that the surface tension of the substrate/composition couple is lower than the surface tension of the substrate/water couple.

2. A process according to claim 1, characterized in that the substrate is a porous absorbent solid body.

3. A process according to claim 1, characterized in that the treatment with the polar substance is carried out before, during or after deposition of the active composition onto the substrate.

4. A process according to claim 1, characterized in that the quantity of polar substance is sufficient for obtaining both conjugated conditions, i.e. polarity and HLB, without modifying substantially either the relative quantities of the constituents of the final system or the essential characteristics of such constituents or their mode of action, in particular, that of the active chemical composition.

5. A process according to claim 1, characterized in that the quantity of polar substance is relatively low in respect to the active composition.

6. A process according to claim 1, characterized in that depending on the initial polarities present and the final polarities to be obtained, the ionic additive compounds are selected from the group consisting of:

compounds containing at least one hetero-atom $P^+$, $O^+$, $S^+$, or $N^+$, and at least one alkyl long chain of at least 8 carbon atoms, such as the quaternary ammonium salts, the imidazoline salts, the phosphonium salts, the oxonium salts, the fatty amines and their derivatives;

compounds containing at least one anionic character group such as the carboxylic, sulfonic, phosphoric, sulfuric group, and at least one alkyl long chain of at least 8 carbon atoms such as alkylphosphonic, alkylsulfuric, alkylsulfonic, alkylcarboxylic acids;

mono or polyfunctional compounds such as organic bases, mineral bases; the compounds of a character at least bifunctional having at least one negative ionic character group and having moreover a positive ionic character higher than those of the ionic group of the support such as monocarboxylic polyamines, peptides, sulfobetaines;

bi or polyfunctional compounds comprising at least two positive ionic groups such as polyamines, quaternary polyammoniums;

compounds comprising at least two negative ionic groups such as polyacids;

mono or polyfunctional compounds such as mineral acids and organic acids; and compounds of a character at least bifunctional having at least one positive ionic character group having moreover a negative ionic character higher than those of the ionic groups of the support such as monoamine polyacids, aminoacids, peptides, sulfobetaines.

7. A composition preventing or delaying desorption by an aqueous medium in a chemical active liquid composition secured to a substrate, said composition being characterized by comprising an absorbing support impregnated with said active composition, and a relatively low quantity of at least one polar ionic compound such as the charges of the support and the active chemical composition are opposite and that the surface tension of the absorbing support and active chemical substance couple is lower than the surface tension of the absorbing support and water couple.

8. A composition according to claim 7, characterized in that the polar ionic compound is selected from the group consisting of compounds containing at least one hereto-atom $P^+$, $O^+$, $S^+$, or $N^+$, and at least one alkyl long chain of at least 8 carbon atoms, such as the quaternary ammonium salts, the imidazoline salts, the phosphonium salts, the oxonium salts, the fatty amines and their derivatives;

compounds containing at least one anionic character group such as the carboxylic, sulfonic, phosphoric, sulfuric group, and at least one alkyl long chain of at least 8 carbon atoms such as alkylphosphonic, alkylsulfuric, alkylsulfonic, alkylcarboxylic acids;

mono or polyfunctional compounds such as organic bases, mineral bases; the compounds of a character at least bifunctional having at least one negative ionic character group and having moreover a positive ionic character higher than those of the ionic group of the support such as monocarboxylic polyamines, peptides, sulfobetaines;

bi or polyfunctional compounds comprising at least two positive ionic groups such as polyamines, quaternary polyammoniums;

compounds comprising at least two negative ionic groups such as polyacids;

mono or polyfunctional compounds such as mineral acids and organic acids; and compounds of a character at least bifunctional having at least one positive ionic character group having moreover a negative ionic character higher than those of the ionic groups of the support such as monoamine polyacids, aminoacids, peptides, sulfobetaines.

9. A composition according to claim 7, characterized in that the chemical active composition is a perfume.

10. A composition according to claim 7, characterized in that the chemical active composition is an insecticide.

11. An application of the process according to claim 1, for the achievement of systems, resisting the effect of water, containing at least one chemical active composition.

12. The application of the process according to claim 1, for the achievement of ambiance deodorants for toilet bowls and insecticides.

13. The application of the composition according to claim 7, to the realization of blocks or plates for insecticides or to ambiance deodorization for toilet bowls.

14. A composition for carrying out the process according to any one of claims 1 to 6, characterized by comprising a chemical liquid active composition containing at least one polar substance compatible with such chemical active composition and and with the substrates onto which it is to be deposited.

15. A composition for carrying out the process according to any one of claims 1 to 6 characterized by consisting of a porous support containing at least one polar substance compatible with such support and with the chemical active composition which such support is intended to carry.

* * * * *